US008374373B2

(12) United States Patent
Sapiejewski et al.

(10) Patent No.: US 8,374,373 B2
(45) Date of Patent: Feb. 12, 2013

(54) HIGH TRANSMISSION LOSS HEADPHONE CUSHION

(75) Inventors: Roman Sapiejewski, Boston, MA (US); Kevin P. Annunziato, Medway, MA (US); Ian M. Collier, Cambridge, MA (US); Jason Harlow, Watertown, MA (US)

(73) Assignee: Bose Corporation, Framingham, MA (US)

(*) Notice: Subject to any disclaimer, the term of this patent is extended or adjusted under 35 U.S.C. 154(b) by 928 days.

(21) Appl. No.: 12/324,336

(22) Filed: Nov. 26, 2008

(65) Prior Publication Data

US 2010/0128884 A1 May 27, 2010

(51) Int. Cl.
*A61F 11/14* (2006.01)
*H04R 25/00* (2006.01)

(52) U.S. Cl. ........ 381/372; 381/371; 381/370; 381/374; 381/71.6; 2/209; 181/129

(58) Field of Classification Search .................... 381/74, 381/309, 87, 71.6, 371, 370, 372, 374; 2/209; 181/129
See application file for complete search history.

(56) References Cited

U.S. PATENT DOCUMENTS

| | | | | |
|---|---|---|---|---|
| 2,336,669 | A * | 12/1943 | Brown et al. | 181/22 |
| 4,856,118 | A * | 8/1989 | Sapiejewski | 2/209 |
| 4,905,322 | A * | 3/1990 | Aileo et al. | 2/209 |
| 6,597,792 | B1 | 7/2003 | Sapiejewski et al. | |
| 7,466,838 | B1 * | 12/2008 | Moseley | 381/370 |
| 2005/0273910 | A1 * | 12/2005 | Cozens et al. | 2/411 |
| 2006/0269090 | A1 * | 11/2006 | Sapiejewski | 381/371 |
| 2009/0110226 | A1 * | 4/2009 | Ishida | 381/370 |
| 2009/0180657 | A1 * | 7/2009 | Isvan | 381/371 |
| 2010/0119076 | A1 * | 5/2010 | Monk et al. | 381/71.6 |

FOREIGN PATENT DOCUMENTS

| | | | |
|---|---|---|---|
| EP | 1417944 | A1 | 5/2004 |
| EP | 1727390 | A2 | 11/2006 |
| EP | 1940197 | A1 | 7/2008 |
| JP | 49027238 | A | 7/1974 |
| JP | 56054702 | A | 5/1981 |
| JP | 62100766 | U | 6/1987 |
| JP | 63232797 | A | 9/1988 |
| JP | 1196999 | A | 8/1989 |
| JP | 2001069590 | A | 3/2001 |
| JP | 2006333483 | A | 12/2006 |

OTHER PUBLICATIONS http://www.earsc.com/HOME/products/CushioningMaterials/CONFORFoams/index.asp?SID=265.*
International Search Report and Written Opinion dated Feb. 10, 2010 for Appl. No. PCT/US2009/065895.
International Search Report and the Written Opinion of the International Searching Authority for PCT/US2012/030683 dated May 24, 2012.

(Continued)

*Primary Examiner* — Matthew Reames
*Assistant Examiner* — Benjamin Tzu-Hung Liu
(74) *Attorney, Agent, or Firm* — Bose Corporation

(57) ABSTRACT

A headset including an earcup having a front opening adapted to be adjacent to the ear of the user, a baffle disposed within the earcup to define front and rear cavities, a cushion extending around the periphery of the front opening of the earcup and constructed and arranged to accommodate the ear of the user, the cushion having a first density, an inner radial portion, and an outer radial portion opposite the inner radial portion, a cushion cover substantially surrounding the cushion to form a headphone cushion assembly, and a high impedance component having a second density and located near the outer radial portion to increase the transmission loss of the cushion along a radial direction.

27 Claims, 15 Drawing Sheets

OTHER PUBLICATIONS

Japanese Office Action dated Aug. 21, 2012 for Japanese Application No. 2011-537738.

European Office Action dated Dec. 17, 2012 for Application No. 09761128.9-2225.

* cited by examiner

HIGH TRANSMISSION LOSS HEADPHONE CUSHION

TECHNICAL FIELD

This description relates to increasing the mechanical or acoustic impedance of a headphone cushion to reduce the audibility of outside sounds without substantially increasing the axial stiffness of the cushion.

BACKGROUND

For background, reference is made to commonly owned U.S. Pat. Nos. 4,922,452 and 6,597,792, the entire contents of which are hereby incorporated by reference.

SUMMARY

In a first aspect, a headset including an earcup having a front opening adapted to be adjacent to the ear of the user, a baffle disposed within the earcup to define front and rear cavities, a cushion extending around the periphery of the front opening of the earcup and constructed and arranged to accommodate the ear of the user, the cushion having a first density, an inner radial portion, and an outer radial portion opposite the inner radial portion, a cushion cover substantially surrounding the cushion to form a headphone cushion assembly, and a high impedance component having a second density and being disposed proximate the outer radial portion to increase the transmission loss of the cushion along a radial direction.

In various embodiments, the headset can include a transducer inside the earcup. The second density can be substantially higher than the first density. In some embodiments the high impedance component is interposed between the outer radial portion of the cushion and the cushion cover. In others embodiments, the high impedance component is interposed between the inner radial portion of the cushion and the cushion cover. In some embodiments, the high impedance component is disposed adjacent the cushion cover. In some embodiments, the high impedance component includes a substantially rigid ring. In still further embodiments, the high impedance component includes a colloidal ring, such as, for example, a gel layer. In some embodiments, the high impedance component includes polyurethane foam. In some embodiments, the cushion cover includes a plurality of openings extending along the inner radial portion of the cushion to acoustically add the volume of the cushion to the volume of the earcup and enhance passive attenuation of the headset. In some embodiments, the cushion cover includes an acoustically transparent mesh along the inner radial portion of the cushion to acoustically add the volume of the cushion to the volume of the earcup and enhance passive attenuation of the headset. In some specific embodiments, the outer radial portion of the cushion has an average area density greater than about 0.03 g/cm$^2$ and the headphone cushion assembly has an axial stiffness per contact area less than about 8 gf/mm/cm$^2$. In some embodiments, the headphone cushion assembly has an axial stiffness per contact area less than about 4 gf/mm/cm$^2$.

The headphone cushion assembly may be a substantially toroidal shape, such as for example, circumaural or is supra-aural. In some embodiments, the headset further includes a microphone inside the earcup adjacent to a driver; and active noise reducing circuitry intercoupling the microphone and the driver constructed and arranged to provide active noise cancellation. In some embodiments, the inner radial portion of the cushion cover is constructed and arranged to furnish additional damping to help smooth an audio response at an ear of a user and control stability when the headset is not being worn on a head of the user. In some embodiments, the cushion cover includes a plurality of openings such that the volume of the cushion is acoustically added to the volume of the earcup. In some specific embodiments, the cushion adheres to the cushion cover with a peel strength greater than about 0.1 gf/mm, and in other embodiments, the foam adheres to the cushion cover with a peel strength greater than about 0.4 gf/mm. In some embodiments, the cushion includes open cell foam and has a bulk density between about 2 pcf and about 6 pcf, and can have an elastic modulus between about 1 kPa and about 10 kPa, or between about 2 kPa and about 5 kPa. In some embodiments, the high impedance component includes a silicone material.

In a second aspect, an apparatus for blocking sound includes an earcup having a front opening adapted to be adjacent the ear of a user; and a headphone cushion assembly extending around the periphery of the front opening of the earcup, the cushion assembly having an inner radial portion, and an outer radial portion opposite the inner radial portion and the ratio of radial stiffness to axial stiffness per contact area of the headphone cushion assembly is greater than about 10 cm$^2$. In some embodiments, a stiffening component is attached to the outer radial portion of the headphone cushion assembly. In still other embodiments, a stiffening component is attached to the outer radial portion of the headphone cushion assembly. In various embodiments, the stiffening component includes a substantially rigid support ring and/or a gel layer. In some embodiments, the headphone cushion assembly may be a substantially toroidal shape.

In another aspect, a headphone cushion assembly includes a cushion comprising an open cell foam and adapted to be adjacent the ear of the user; an inner cushion cover substantially covering the inner portion of the cushion proximate the ear of the user; the inner cushion cover comprising a plurality of openings, and an outer cushion cover substantially covering the outer part of the cushion distal to the ear of the user, the outer cushion cover comprising a first layer having an average area density less than about 0.03 g/cm$^2$ and a second layer attached to the first layer, the second layer having an average area density greater than about 0.045 g/cm$^2$.

DETAILED DESCRIPTION

Figure 1:
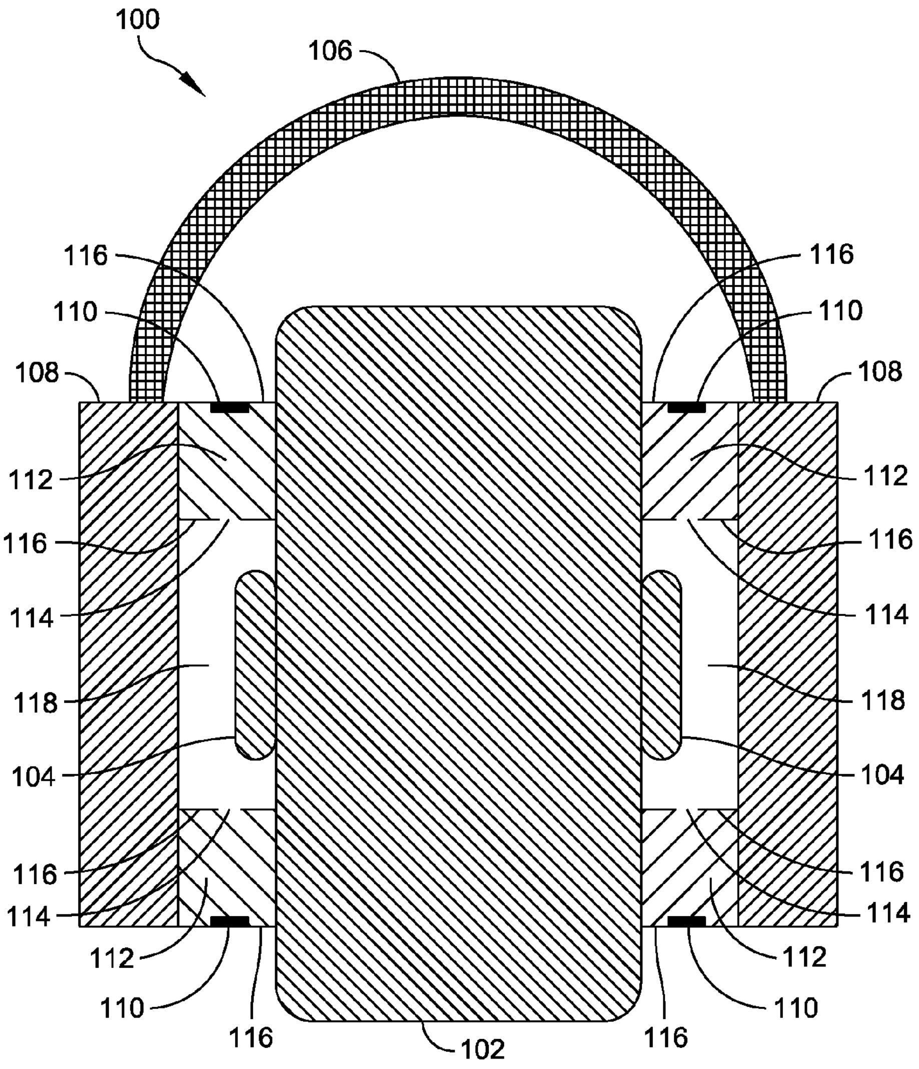
FIG. 1 is a diagrammatic view of a headphone assembly on a head.

Referring to FIG. 1, there is shown a diagrammatic view one embodiment of a headphone assembly 100 worn by a user on a human head 102 having ears 104. The headphone assembly 100 includes suspension assembly 106, transducer assembly 108, stiffening component 110, headphone cushion 112, audio opening 114, and cover 116. Headphone assembly 100 is shown covering and substantially surrounding ears 104 and accordingly, is referred to as circumaural headphones. Alternatively, headphone assembly 100 may be an on-the-ear (supra-aural) set of headphones. Stiffening component 110 serves to increase the impedance of the outer cover of the cushion thus reducing the sound transmission through headphone assembly 110, thereby improving the isolation from outside noise for the headphones listener. In some embodiments, the stiffening component does not appreciable change the axial stiffness of the cushion so as not to impact the comfort of the headphone assembly to the user. An earcup assembly is formed by the combination of transducer assembly 108, headphone cushion 112, and cover 116. Optionally, stiffening component 110 may be included in the earcup assembly. The earcup assembly may have a substantially toroidal shape to fit over or on the ear 104.

The stiffening component 110 may be shaped in the form of a support ring that encircles the headphone cushion 112. Cover 116 may extend over the exterior portion of headphone cushion 112. Cover 116 may extend over the interior portion of headphone cushion 112. Interior cavity 118 is formed by transducer assembly 108, headphone cushion 112, and head 102. Headphone cushion 112 may be constructed of open cell foam. If headphone cushion 112 is constructed of open cell foam, audio openings 114 allow the volume of the headphone cushion 112 to combine with interior volume 118. This combined volume is useful for tuning the audio characteristics of headphone assembly 100. Audio openings 114 are constructed and arranged to furnish additional damping to help smooth the audio response of headphone assembly 100 and control stability when headphone assembly 100 is not being worn. For a description of tuning using audio openings and combined volume, reference is made to U.S. Pat. Nos. 4,922,542 and 6,597,792.

The bulk density of foam is defined as the density of the foam in its expanded state. In some implementations, headphone cushion 112 may have a bulk density of about 2 to about 6 pounds-mass per cubic foot (pcf). In one implementation, the headphone cushion 112 includes a foam having a bulk density of about 5 pcf. In some implementations, the headphone cushion 112 includes a foam having an elastic modulus between 1 and 10 kiloPascals (kPa). In one implementation, the headphone cushion 112 includes a foam having an elastic modulus between about 2 and about 5 kPa. High stiffness foam is useful to reduce sound transmission through headphone cushion 112. However, foam that is too stiff may reduce the comfort of the headphones.

Figure 2A:
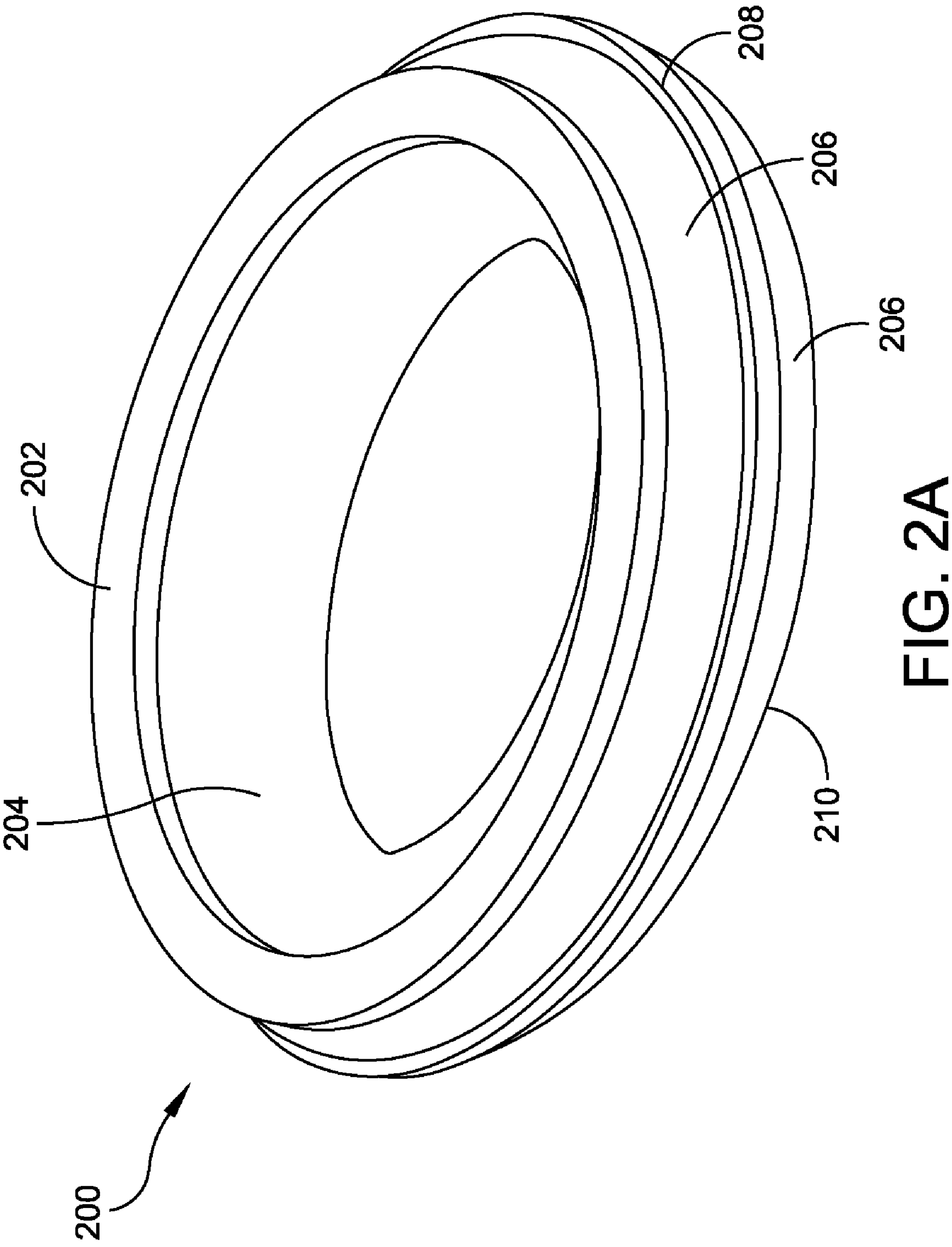
FIG. 2A is a perspective drawing of one embodiment of a headphone cushion including a stiffening component and FIG. 2B is plan view of one embodiment of a headphone cushion.
Figure 2B:
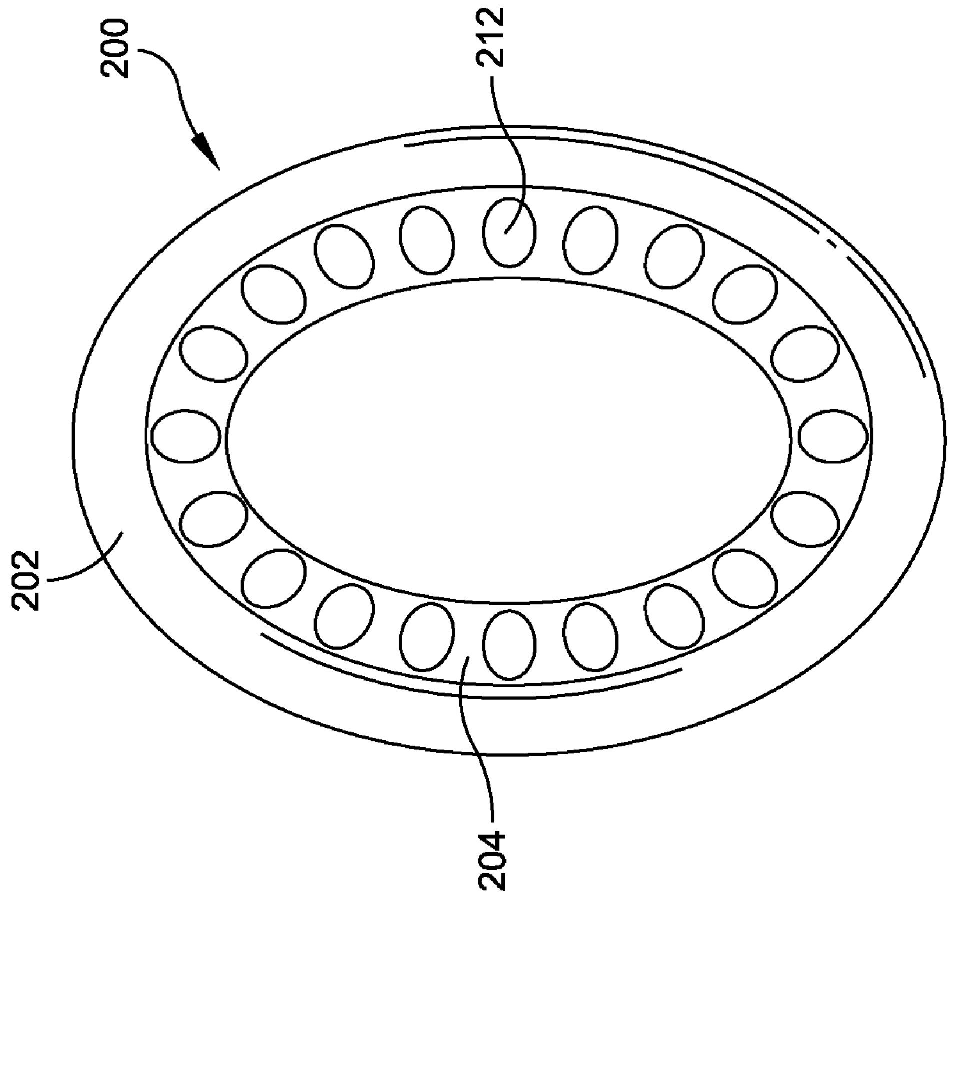

Referring to FIGS. 2A and 2B, in one embodiment of a headphone cushion assembly 200 includes gasket 202, inside cover 204, outside cover 206, stiffening ring 208, and front surface 210. The headphone cushion assembly for only one ear is depicted but it is understood by persons of ordinary skill in the art that headphone cushion assemblies for two ears are included in a set of headphones. Front surface 210 fits against the head of the listener while the headphone is in use. Gasket 202 fits between the headphone cushion assembly 200 and transducer assembly 108 to affect a seal at the interface. Inside cover 204 and outside cover 206 may be one continuous piece of material in some embodiments. Inside cover 204 and outside cover 206 may be made of plastic, leather, leatherette, or leather-like plastic (also known as pleather) material. In FIG. 2A, stiffening ring 208 is attached to the outside of outside cover 206. Alternatively, stiffening ring 208 may be attached to the inside of outside cover 206. Headphone cushion assembly 200 may have a substantially toroidal shape to fit over or on the shape of the human ear. In some embodiments, the headphone cushion assembly 200 further includes a plurality of openings 212 (FIG. 2B) disposed along the inside cover 204 to expose the underlying foam and thereby increase the effective volume of the earcup by the volume of the underlying foam. In these embodiments, passive attenuation is enhanced and additional damping is provided to help smooth the audio response and control stability of the feedback loop of the active noise reduction system, as more fully explained in commonly owned U.S. Pat. No. 6,597,792.

Figure 3:
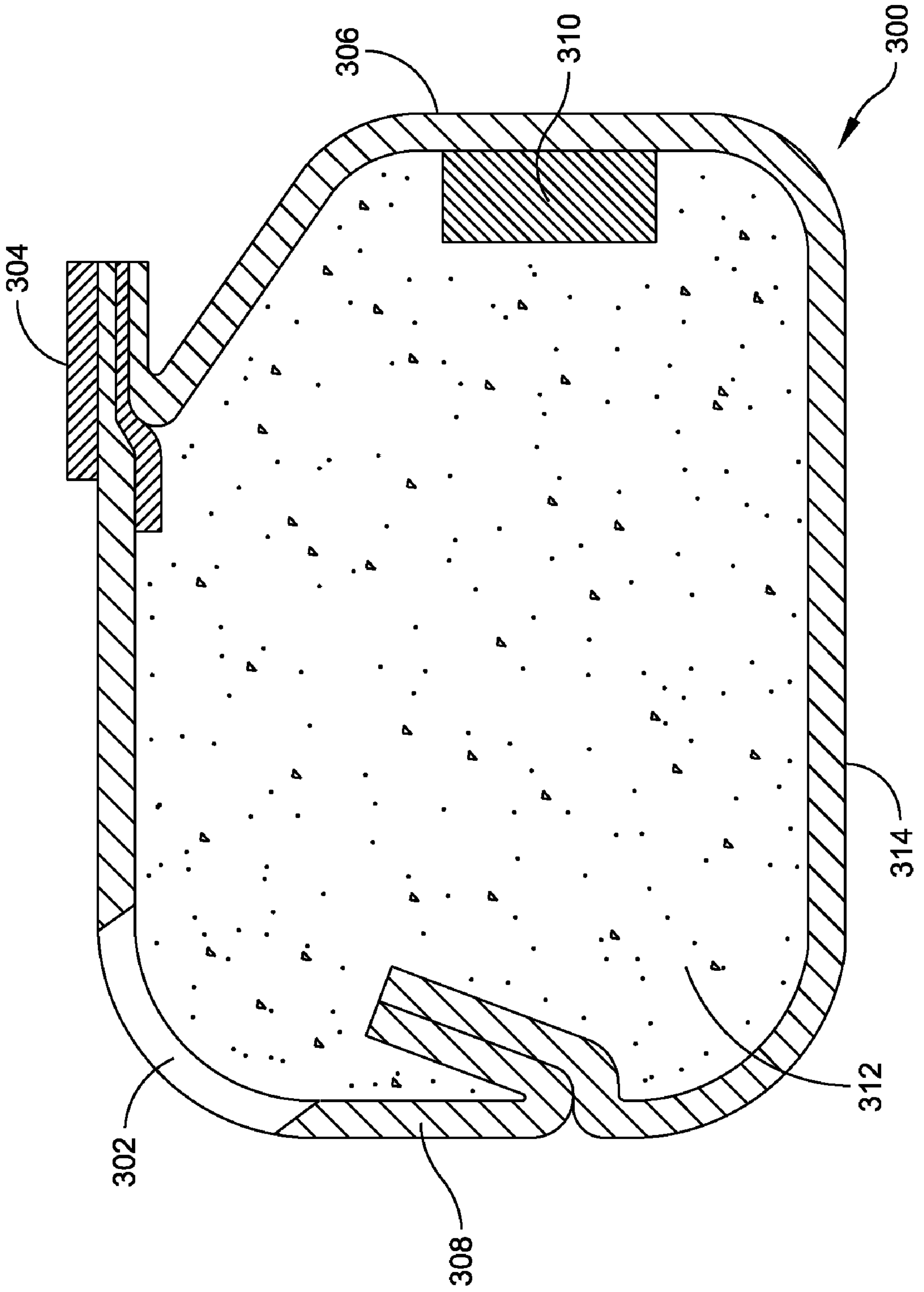
FIG. 3 is a sectional view of a headphone cushion including a stiffening ring.

Referring to FIG. 3, there is shown a section drawing of another embodiment of a headphone cushion assembly. In FIG. 3, Headphone cushion assembly 300 includes opening 302, gasket 304, outside cover 306, inside cover 308, stiffening ring 310, headphone cushion 312, and front surface 314. In this embodiment, stiffening ring 310 is attached to the inside of outside cover 306.

The radial stiffness of headphone cushion assembly 300 is measured by compressing one side of headphone cushion assembly 300 in a direction along the radius of it's toroidal shape and measuring the force necessary to compress headphone cushion assembly 300 a known distance. Stiffness is calculated by dividing the force by the distance compressed. Likewise, the axial stiffness is calculated in a direction along the axis of the toroidal shape. The radial directions are perpendicular to the axial direction. To achieve high attenuation simultaneously with good comfort, the ratio of radial stiffness to axial stiffness per contact area should be greater than 10 $cm^2$.

Figure 4:
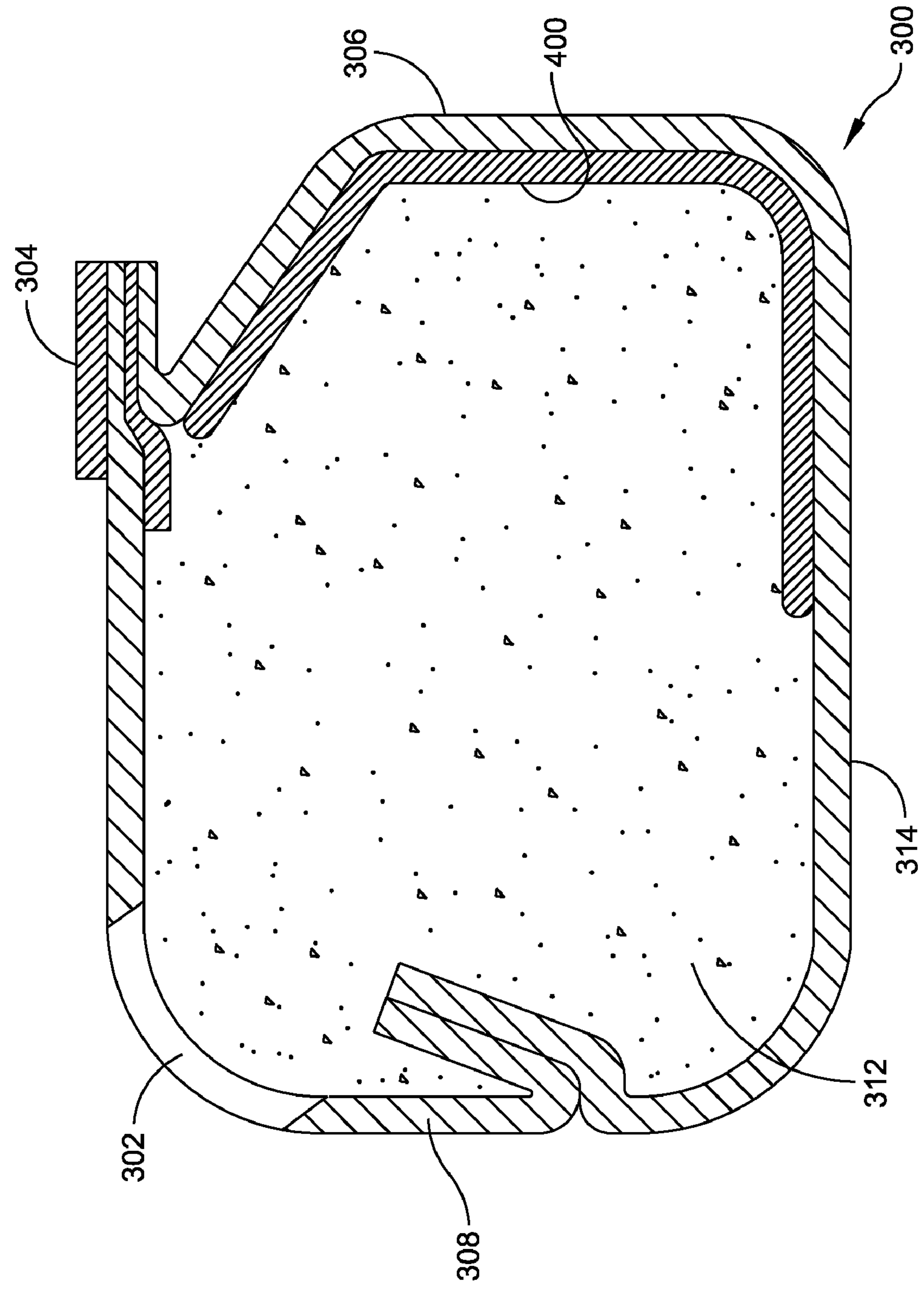
FIG. 4 is a sectional view of a headphone cushion including a high density layer.

Referring to FIG. 4, there is shown a section drawing of another embodiment of a headphone cushion assembly. To increase the mechanical impedance of the outer cushion cover, a high density layer 400 is attached to the inside of outside cover 306. Outside cover 306 forms a first layer. High density layer 400 forms a second layer. In one embodiment, outside cover 306 has an average area density of less than 0.03 $g/cm^2$ and high density layer 400 has an average area density greater than 0.045 $g/cm^2$. The high density layer may be a highly compliant, massive, and dissipative material. The high density layer may be silicone gel. The high density layer may optionally be applied to only the outside of outside cover 306 or to both the inside and outside of outside cover 306.

Figure 5:
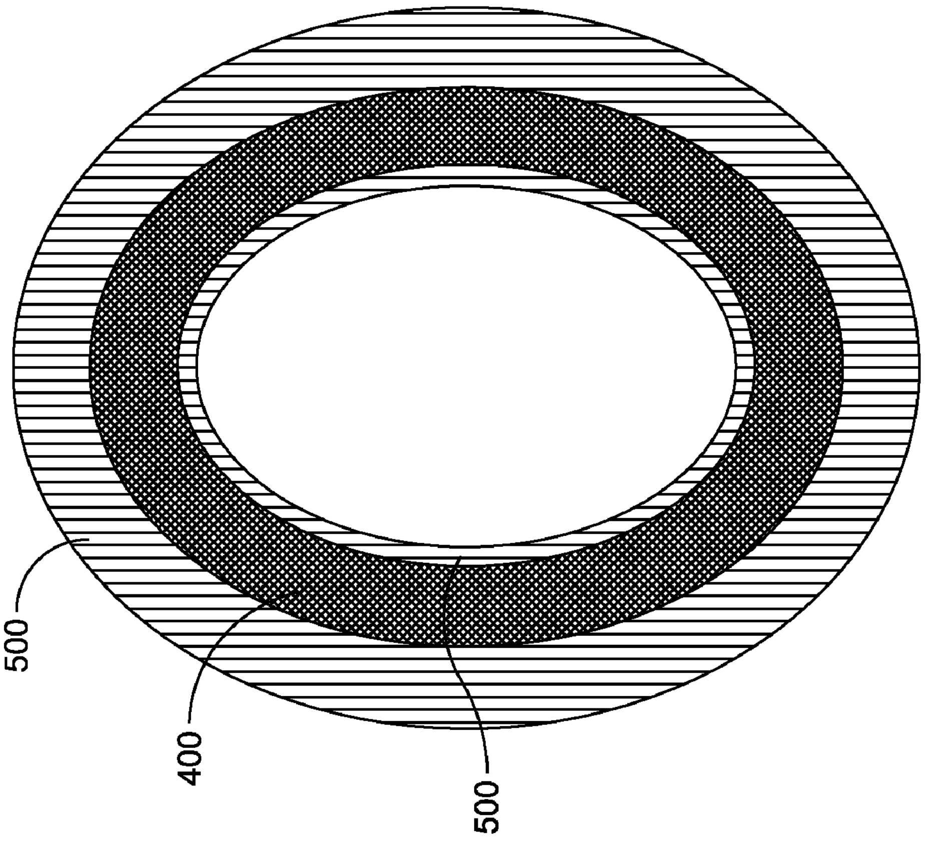
FIG. 5 is a drawing of an outer cover including a high density layer.

Referring to FIG. 5, there is shown a headphone cushion cover before it is spread around a headphone cushion. In this state, the headphone cushion cover is a flat piece of cloth or similar material shown as cover 500. High density layer 400 is shown attached to cover 500. The average area density is defined as the mass per unit area averaged over the area shown in FIG. 5. For example, the average area density of cover 500 is the total mass of cover 500 divided by the area of cover 500 as shown in FIG. 5. The average area density of high density layer 400 is the total mass of high density later 400 divided by the area of layer 400 as shown in FIG. 5.

Figure 6:
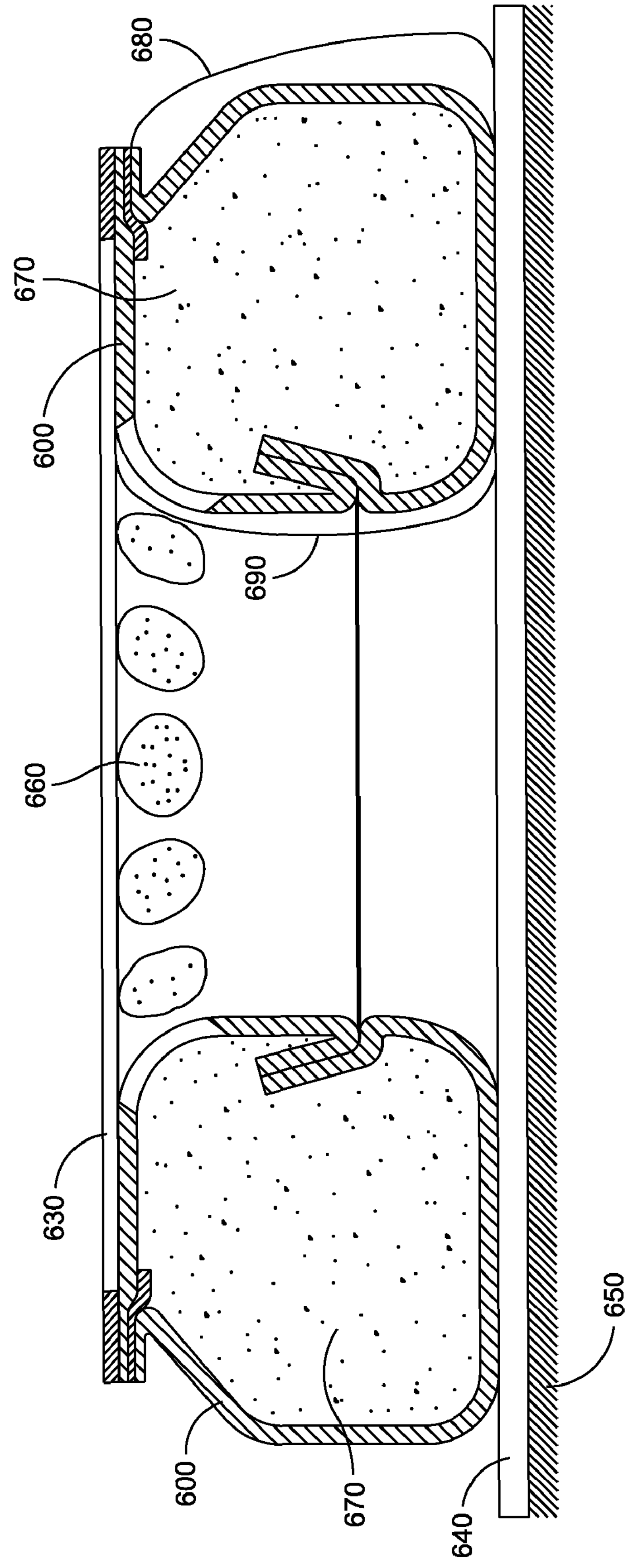
FIG. 6 is a sectional view of an earcup assembly.

Referring to FIG. 6, there is shown a section drawing of a headphone cushion assembly pressed between top plate 630 and bottom plate 640. Bottom plate 640 is immovable as shown by hash marks 650. Cover 600 covers cushion 670. Outside portion 680 of cover 600 is outside of the headphone cushion assembly and extends from the contact point between cover 600 and top plate 630 to the contact point between cover 600 and bottom plate 640. Inside portion 690 of cushion 600 is inside of the headphone cushion assembly and extends from the contact point between cover 600 and top plate 630 to the contact point between cover 600 and bottom plate 640. Audio openings 660 are also shown in cover 600.

In one embodiment, the headphone assembly has audio openings in the portion of the cover that extends over the interior surface of the headphone cushion. The audio openings function to acoustically add the volume of the headphone cushion 112 to the interior volume 118 which enhances passive attenuation. The audio openings are approximately 30% of the total surface area of the interior surface of the cover. The approximate volume of the interior cavity is 100 cc, the half-mass of the headphone assembly is 95 g, and the stiffness of the headphone cushion is 100 g-force/mm. The approximate volume of the open-cell foam in the headphone cushion is 40 cc, so the combined volume of the interior cavity and headphone cushion is 140 cc.

At frequencies above the resonance of the axial bouncing mode of the headphone, a second mode of radial, through-cushion transmission may exist—especially in low-impedance cushions with audio openings. Increased radial stiffness through the addition of a stiffening ring, or increased mass and damping through the application of a silicone gel can improve the cushion's attenuation of outside noise. Increased cushion cover stiffness, mass, and damping generally correlate with higher attenuation. The axial stiffness affects the comfort of the headphones. Low axial stiffness is desired to improve comfort. For a headphone cushion assembly without a stiffening ring, the axial stiffness is approximately 80 gf/mm. For the same headphone cushion with a stiffening ring, the axial stiffness is approximately 100 gf/mm. The stiffening ring increases the radial stiffness much more than the axial stiffness. This difference in stiffness creates headphones that have both excellent comfort and high attenuation of outside noise.

Figure 7:
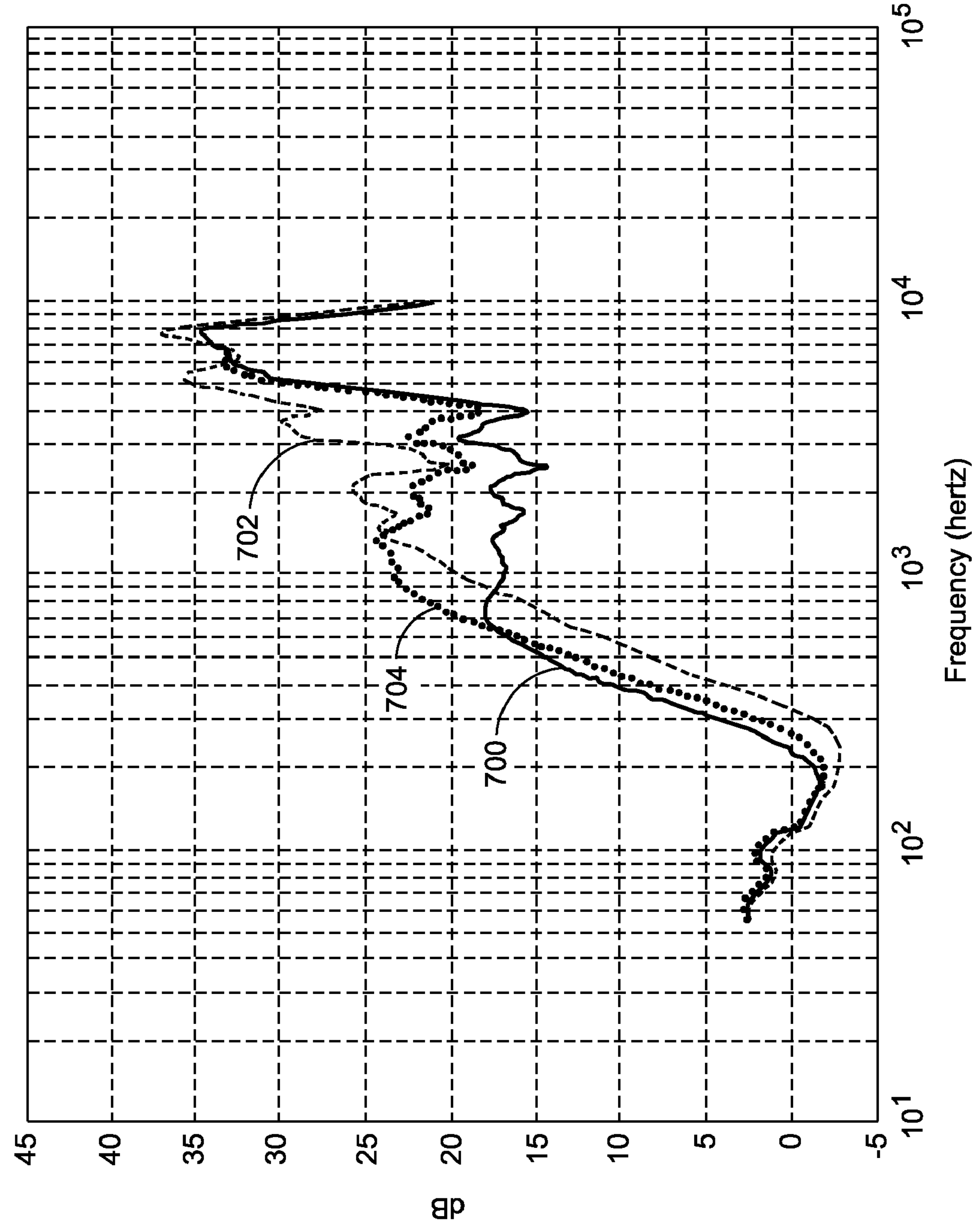
FIG. 7 is a graph of sound attenuation through a headphone assembly including a stiffening ring as measured on a test fixture.

Referring to FIG. 7, there is shown a graph of measured sound attenuation (in dB) vs frequency (in Hertz) through one embodiment of a headphone assembly while the headphone assembly is mounted on a test fixture. As opposed to the human head, the test fixture is flat so that it does not have leaks between the headphone cushion and the test fixture. Also, the fixture is rigid compared with the much more compliant surface (the skin) of a human test subject. The shapes of the curves in FIG. 7 depend on the physical dimensions and material properties of the headphone assembly under test. Curve 700 shows the sound attenuation through a headphone assembly that has an exterior cover over the headphone cushion, but no interior cover. Curve 702 shows the sound attenuation through a headphone assembly that has both an exterior cover and an interior cover over the headphone cushion. Curve 704 shows the sound attenuation through a headphone assembly that has an exterior cover over the headphone cushion, holes in the interior cover (or no interior cover), and a stiffening ring attached to the outside of the exterior cover. Curve 704 shows the benefit of high attenuation from the stiffening ring above approximately 500 Hz. The attenuation of the headphones with the stiffening ring and holes in the interior cover is approximately equal to the attenuation from the headphone assembly with both inside and outside covers. The advantage of using holes in the interior cover and the stiffening ring rather than interior and exterior covers is that the volume of the headphone cushion can be used to help tune the audio characteristics of the headphones. Since the volume encapsulated by the cushion may be utilized, the headphone assembly may be made smaller and still achieve performance similar to a larger set of headphones that has no holes in the interior cover.

Figure 8:
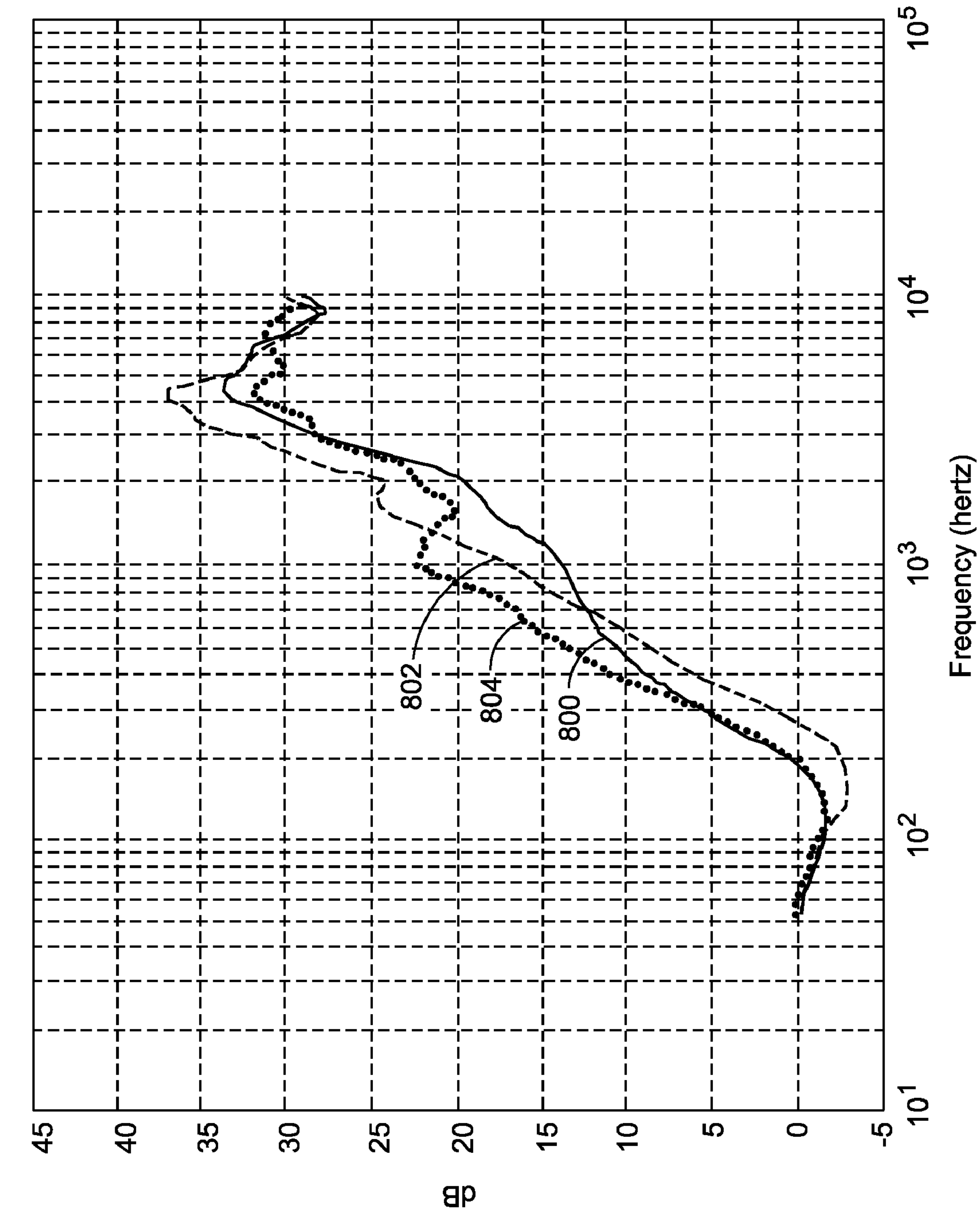
FIG. 8 is a graph of sound attenuation through a headphone assembly including a stiffening ring as measured on a head.

Referring to FIG. 8, there is shown a graph of measured sound attenuation (in dB) vs frequency (in Hertz) through one embodiment of a headphone assembly while the headphone assembly is mounted on human heads. The curves in FIG. 8 represent data averaged from many individual heads. The set of headphones does not perfectly fit on each head, so leaks occur between the set of headphones and the heads. The shapes of the curves in FIG. 8 depend on the physical dimensions of the heads, and the physical dimensions and material properties of the set of headphones under test. Curve 800 shows the sound attenuation through a set of headphones that has an exterior cover over the headphone cushion, but no interior cover. Curve 802 shows the sound attenuation through a set of headphones that has both an exterior cover and an interior cover over the headphone cushion. Curve 804 shows the sound attenuation through a headphone assembly that has an exterior cover over the headphone cushion, holes in the interior cover (or no interior cover), and a stiffening ring attached to the outside of the exterior cover. Curve 804 shows the benefit of high attenuation from the stiffening ring above approximately 500 Hz.

Figure 9:
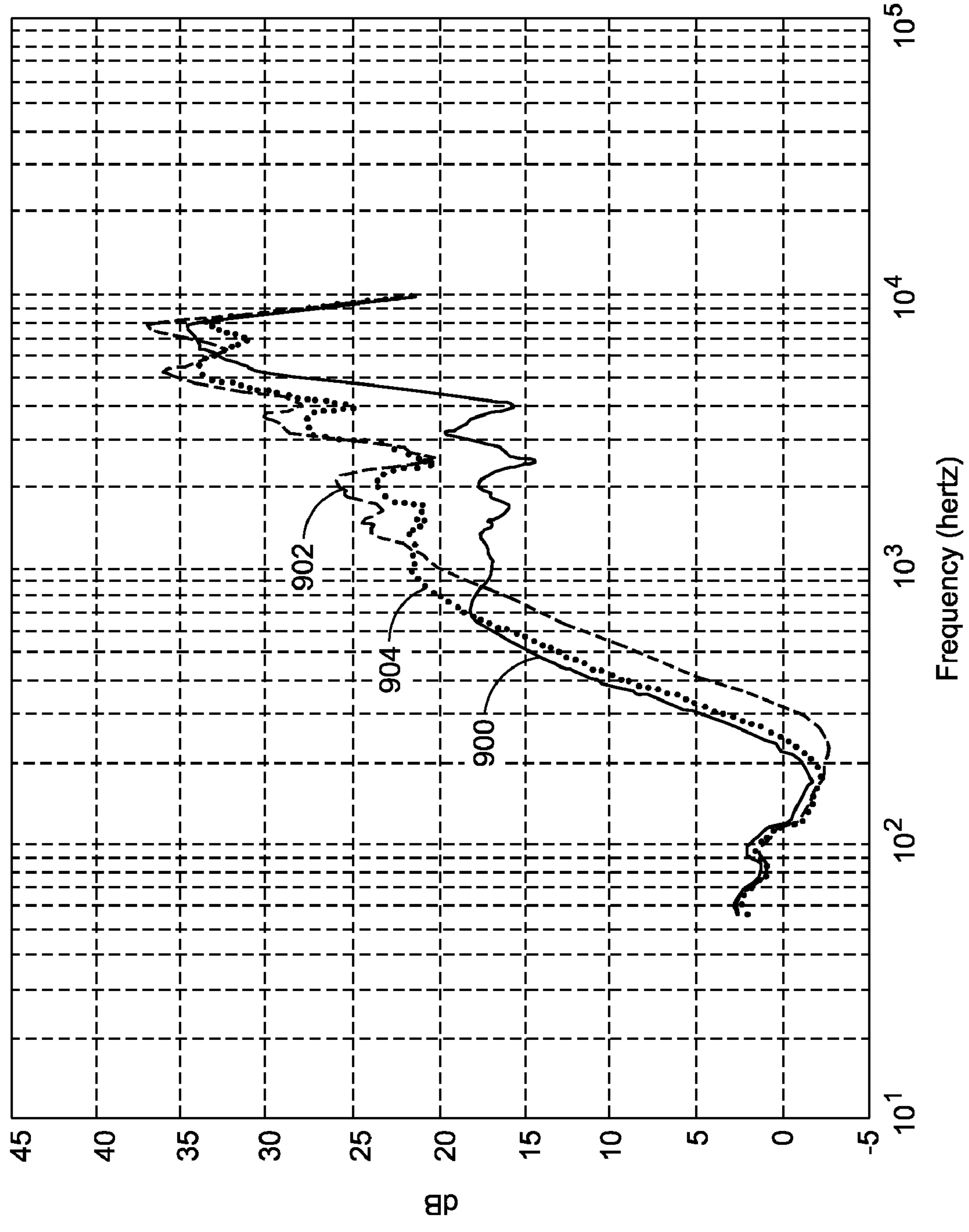
FIG. 9 is a graph of sound attenuation through a headphone assembly including a high density layer as measured on a test fixture.

Referring to FIG. 9, there is shown a graph of measured sound attenuation (in dB) vs frequency (in Hertz) through one embodiment of a headphone assembly while the headphone assembly is mounted on a test fixture. The shapes of the curves in FIG. 9 depend on the physical dimensions and material properties of the headphone assembly under test. Curve 900 shows the sound attenuation through a headphone assembly that has an exterior cover over the headphone cushion, but no interior cover. Curve 902 shows the sound attenuation through a headphone assembly that has both an exterior cover and an interior cover over the headphone cushion. Curve 904 shows the sound attenuation through a headphone assembly that has an exterior cover over the headphone cushion, holes in the interior cover (or no interior cover), and a high density layer attached to the inside of the exterior cover. Curve 904 shows the benefit of high attenuation from the high density layer above approximately 500 Hz. The attenuation of the headphones with the high density layer and holes in the interior cover is approximately equal to the attenuation from the headphone assembly with both inside and outside covers.

Figure 10:
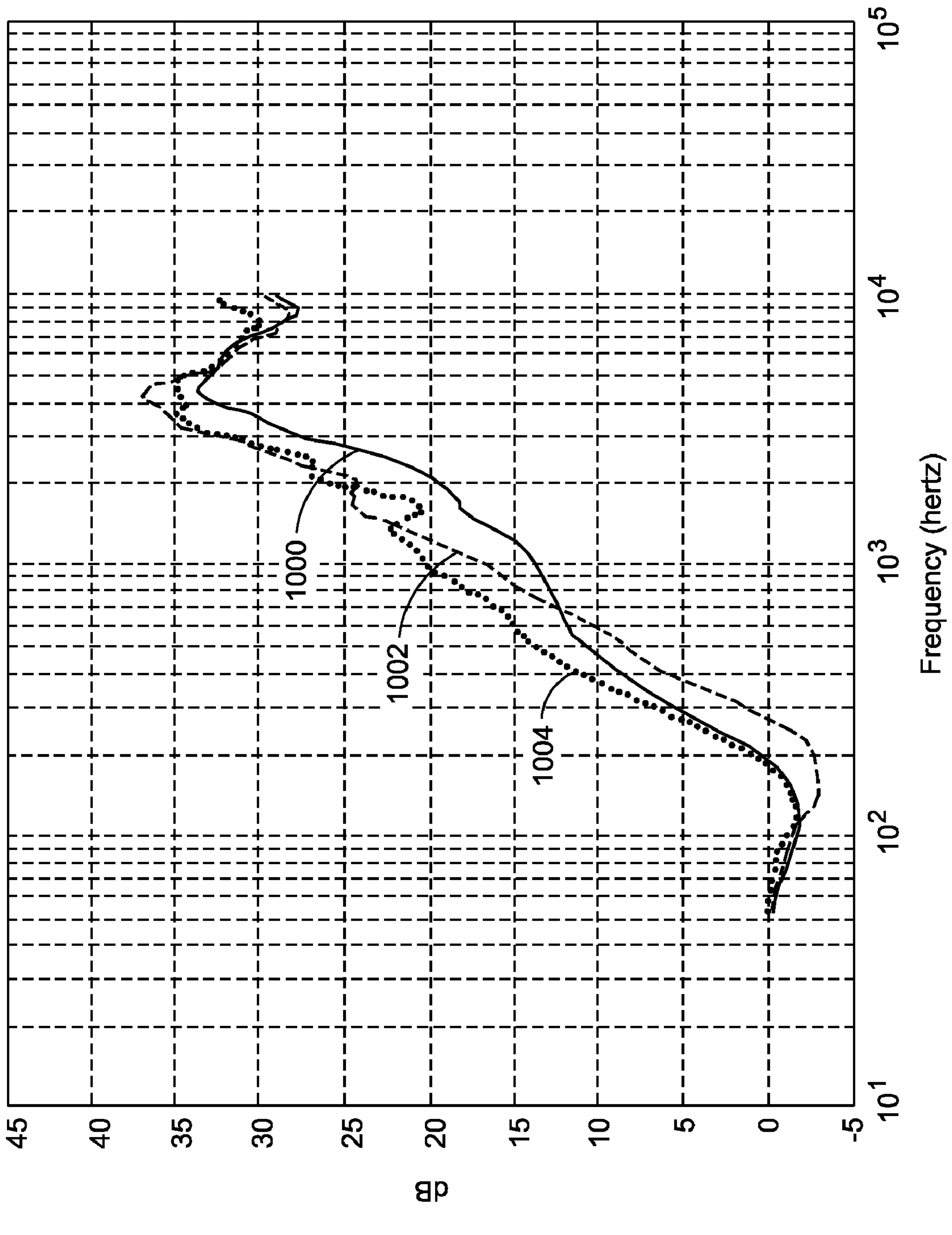
FIG. 10 is a graph of sound attenuation through a headphone assembly including a high density layer as measured on a head.

Referring to FIG. 10, there is shown a graph of measured sound attenuation (in dB) vs frequency (in Hertz) through one embodiment of a headphone assembly while the headphone assembly is mounted on human heads. The curves in FIG. 10 represent data averaged from many individual heads. The shapes of the curves in FIG. 10 depend on the physical dimensions of the heads, and the physical dimensions and material properties of the set of headphones under test. Curve 1000 shows the sound attenuation through a set of headphones that has an exterior cover over the headphone cushion, but no interior cover. Curve 1002 shows the sound attenuation through a set of headphones that has both an exterior cover and an interior cover over the headphone cushion. Curve 1004 shows the sound attenuation through a headphone assembly that has an exterior cover over the headphone cushion, holes in the interior cover (or no interior cover), and a high density layer attached to the inside of the exterior cover. Curve 1004 shows the benefit of high attenuation from the high density layer above approximately 500 Hz.

Figure 11:
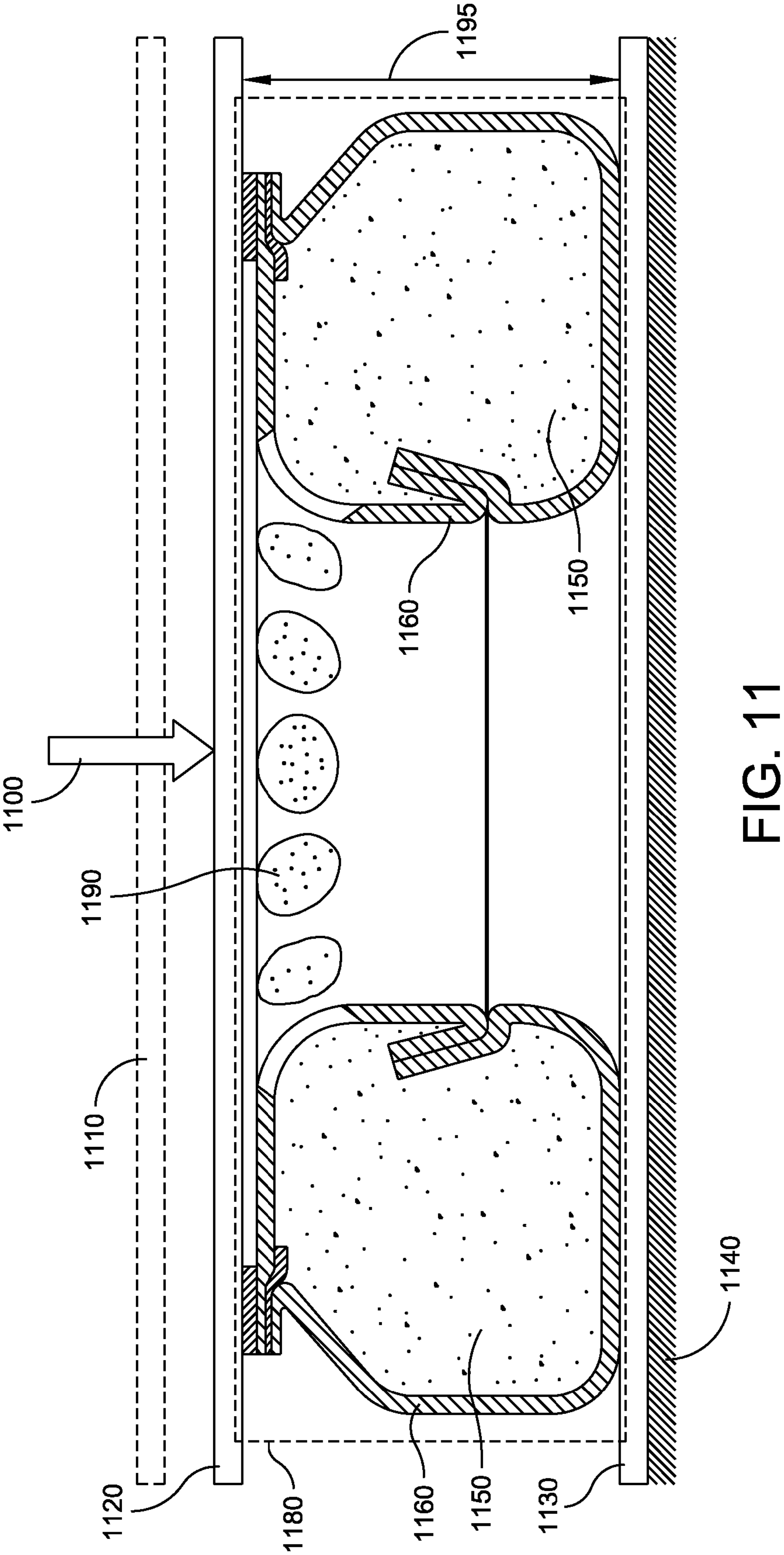
FIG. 11 is a sectional view of a test method for measuring axial stiffness.

Referring to FIG. 11, there is shown a sectional view of a test method for axial stiffness. Force 1100 is applied to moveable plate 1110 which pushes on top plate 1120. Bottom plate 1130 is held immovable as shown by hash marks 1140. Headphone cushion assembly 1180 includes cushion 1150, cover 1160, and attachment plate 1170. Headphone cushion assembly 1180 is pressed between top plate 1120 and bottom plate 1130 during the axial stiffness test. Distance 1195 is the distance between top plate 1120 and bottom plate 1130. Audio openings 1190 are also shown in cover 1160. The steps of the axial stiffness test procedure are as follows. Determine the nominal clamp force of a headset (adjusted for medium size) as the force applied by the ear cushions to parallel plates with outer surfaces spaced 138 mm apart. Place headphone cushion assembly 1180 between top plate 1120 and bottom plate 1130. Apply a series of known forces 1100 to top plate 1120 in the direction perpendicular to top plate 1120. The range of forces 1100 should include the nominal clamp force of the corresponding headset. Record the resulting distances 1195 and forces 1100. Calculate the axial stiffness of the headphone cushion assembly as the slope of the forces 1100 as a function of distances 1195 in gf/mm at the nominal clamp force of the corresponding headset. Determine the contact area of the headphone cushion assembly as the total area of cover 1160 which is in contact with bottom plate 1130 when the nominal clamp force of the corresponding headset is applied as force 1100. Calculate the axial stiffness per contact area as the axial stiffness divided by the contact area of the cushion in $gf/mm/cm^2$. Forces 1100 should be applied at less than or equal to 100 gf/min. Alternatively, forces 1100 may be applied rapidly if two minutes settling time is allowed before measurement of the forces 1100 and distances 1195.

Figure 12:
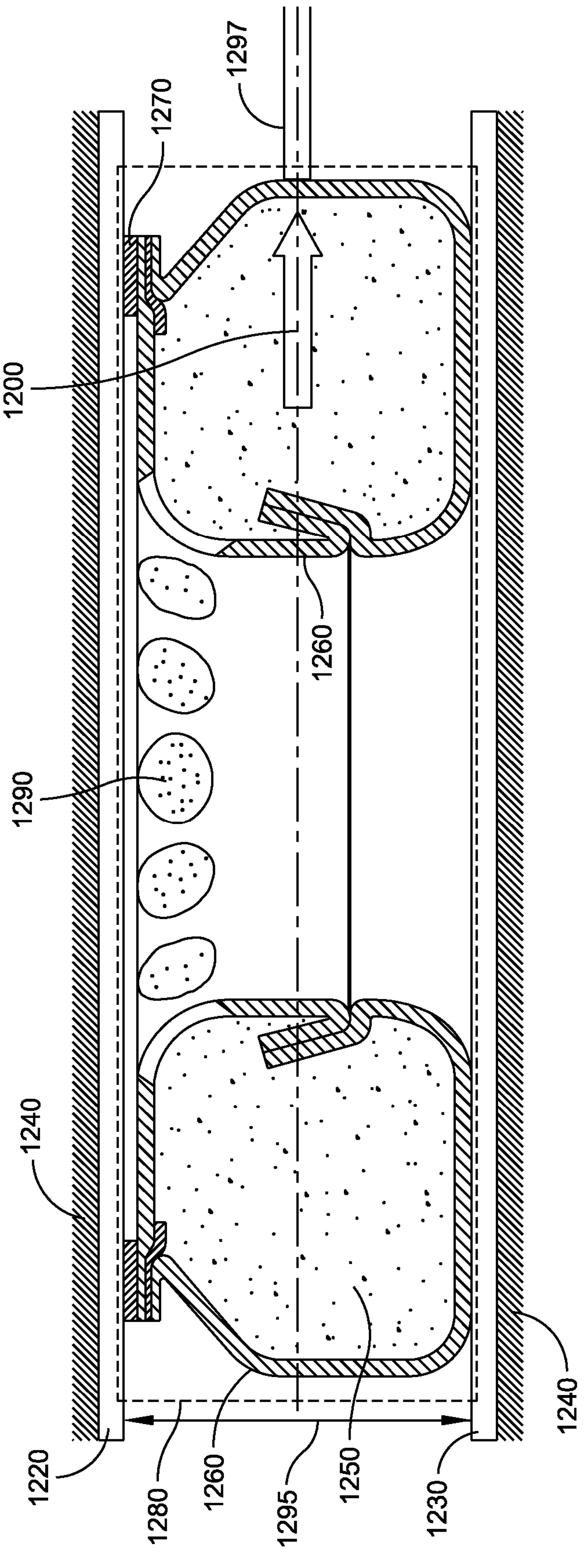
FIG. 12 is a sectional view of a test method for measuring radial stiffness.

Referring to FIG. 12, there is shown a sectional view of a test method for radial stiffness. Top plate 1220 and bottom plate 1230 are held immovable as shown by hash marks 1240. Headphone cushion assembly 1280 includes cushion 1250, cover 1260, and attachment plate 1270. Top plate 1220 and bottom plate 1230 have adhesive surfaces to hold headphone cushion assembly 1280 in place between top plate 1220 and bottom plate 1230. Distance 1295 is the distance between top plate 1220 and bottom plate 1230. Indenter 1297 pushes on the headphone cushion assembly in a radial direction. Indenter 1297 is a rigid cylinder with a diameter of 3 mm. Resultant force 1200 pushes back on indenter 1297. Audio openings 1290 are also shown in cover 1260. Before the radial test procedure is performed, distance 1295 must be determined. Using the test setup in FIG. 11, set force 1100 to 150 gf and measure resultant distance 1195. Set distance 1295 in FIG. 12 equal to resultant distance 1195 from the test setup in FIG. 11 with force 1100 equal to 150 gf. The steps of the radial stiffness test procedure are as follows. Clamp headphone cushion assembly 1280 between top plate 1220 and bottom plate 1230. Position the axis of indenter 1297 in the central plane of cushion 1250, and along a direction perpendicular to the curvature of the cover 1260's outer surface when viewed along a direction perpendicular to plates 1220 and 1230. Push indenter 1297 3.8 mm (from the position of initial contact) into headphone cushion assembly 1280. After 2 minutes settling time, record the resultant force 1200 on indenter 1297. Calculate the radial stiffness of the headphone cushion assembly as the resultant force 1200 divided by the 3.8 mm indenting distance in gf/mm.

Figure 13:
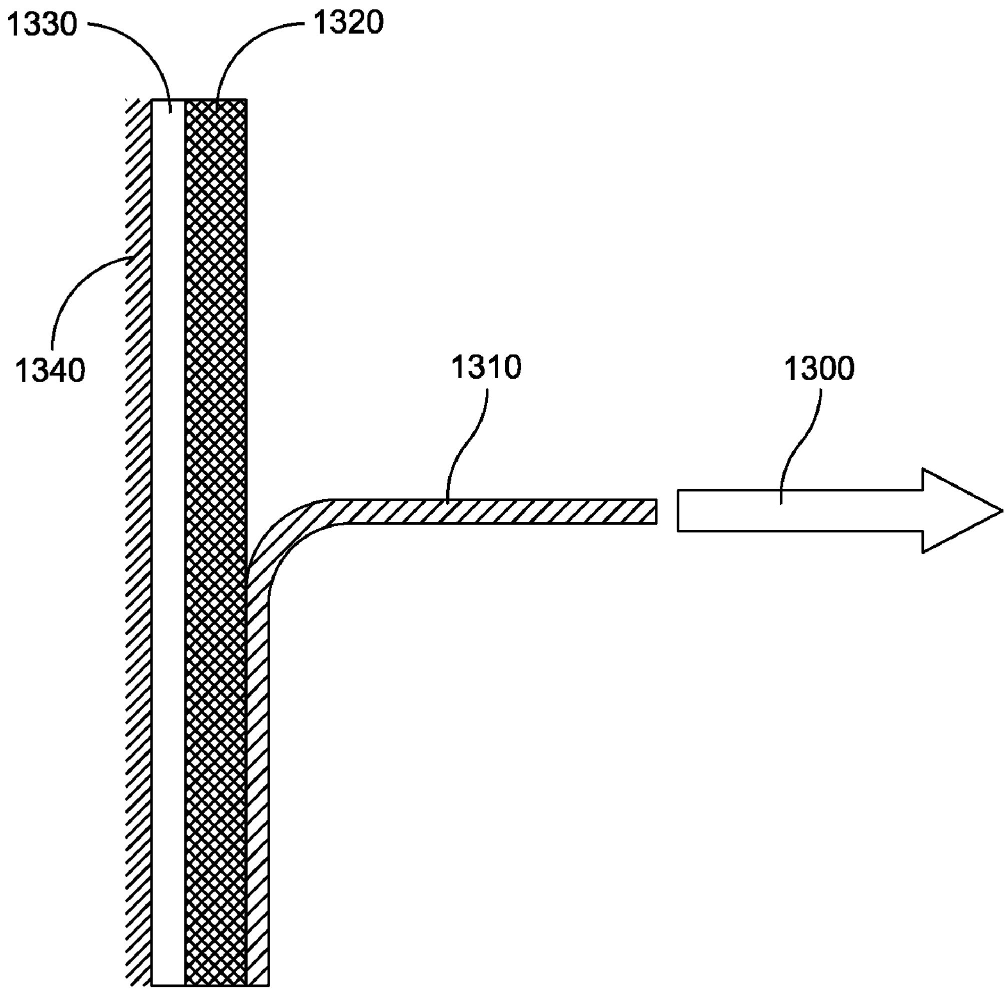
FIG. 13 is a sectional view of a test method for measuring peel strength.

Referring to FIG. 13, there is shown a sectional view of a test method for peel strength. Force 1300 is applied to pull up cover sample 1310 from foam sample 1320. Foam sample 1320 is mounted to plate 1330 which is held immovable as shown by hash marks 1340. Cover sample 1310 is a rectangular piece of outer cover material from the headphone cushion assembly with a width greater than 100 mm and a length greater than 150 mm. Foam sample 1320 is a rectangular piece of foam from the headphone cushion assembly which has a width and length larger than cover sample 1310. Cover sample 1310 is placed over foam sample 1320 such that the inner surface of cover 1310 contacts foam sample 1320. 10 kPa of force is then applied evenly to cover sample 1310 on foam sample 1320 for 2 minutes to allow cover sample 1310 to adhere to foam sample 1320. The steps of the peel strength test procedure are as follows. Using a load cell with a resolution of at least 0.01 N to measure force 1300, peel cover sample 1310 from foam sample 1320 at a rate of 60 mm/min in the direction perpendicular to foam sample 1320. According to one test protocol, cover sample 1310 can be peeled so that the angle between cover sample 1310 and foam sample 1320 remains within 10° of perpendicular. Record average force 1300 as the average force measured over a peel distance of 100 mm. The peel direction should be perpendicular to the direction of gravity. Calculate the peel strength as average force 1300 divided by the width of the cover sample 1310 in gf/mm.

Figure 14:
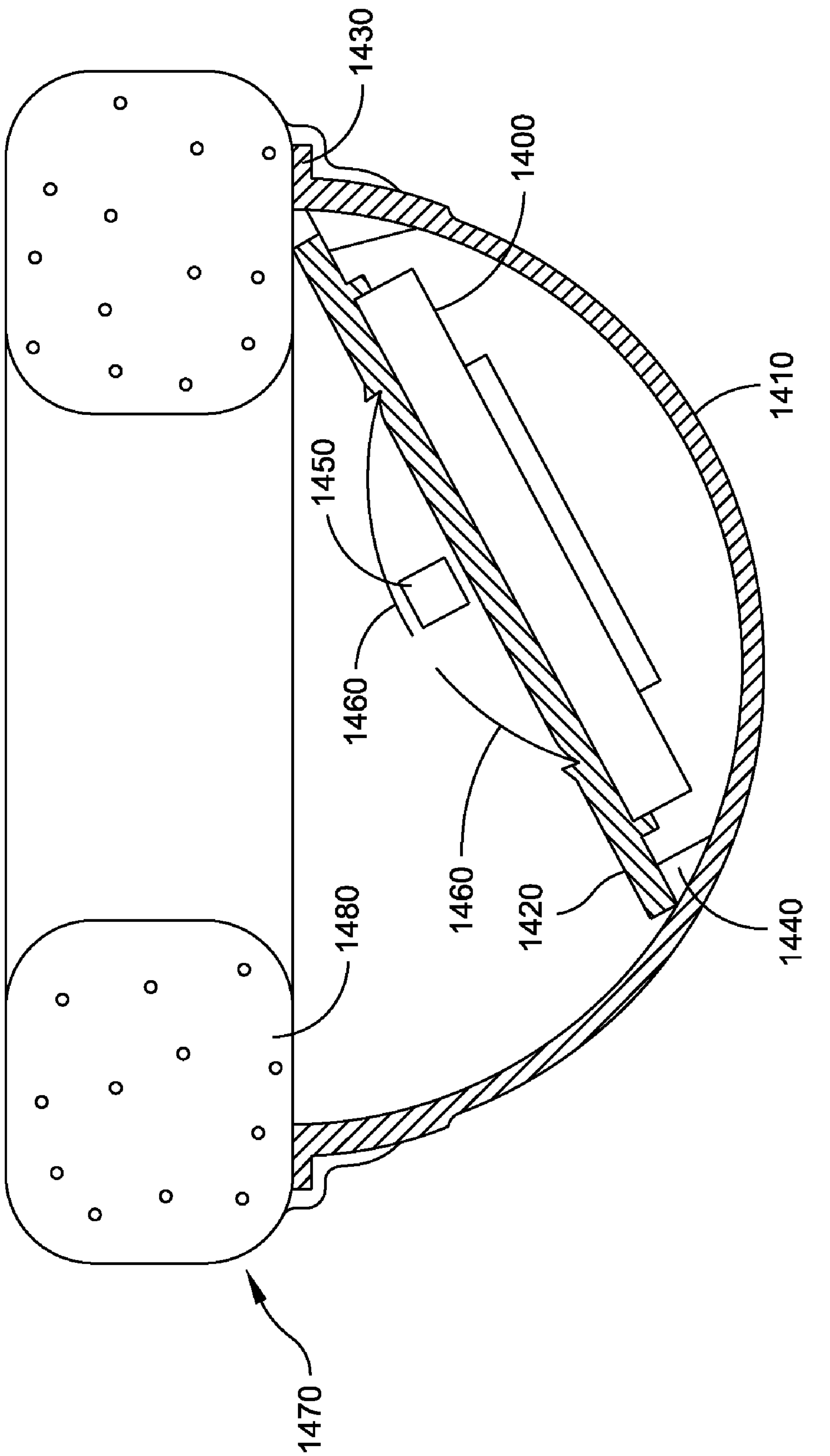
FIG. 14 is a sectional view of an earcup assembly including active noise reducing circuitry.

Referring to FIG. 14, there is shown a sectional view of an earcup assembly with noise reducing circuitry. Reference is made to U.S. Pat. No. 6,597,792, the entire contents of which are hereby incorporated by reference. Driver 1400 is seated in earcup 1410 with driver plate 1420 extending rearward from a lip 1430 of earcup 1410 to a ridge 1440 with microphone 1450 closely adjacent to driver 1400 and covered by a wire mesh resistive cover 1460. Cushion 1470 covers the front opening of earcup 1410 and includes foam 1480.

Other implementations are also within the scope of the following claims.

What is claimed is:

1. A headset comprising:

an earcup having a front opening adapted to be adjacent to the ear of the user;

a baffle disposed within the earcup to define front and rear cavities;

a cushion extending around the periphery of the front opening of the earcup and constructed and arranged to accommodate the ear of the user, the cushion having a first density, an inner radial portion, and an outer radial portion opposite the inner radial portion;

a cushion cover substantially surrounding the cushion to form a headphone cushion assembly; and a high impedance component having a second density and being disposed radially outward from the cushion, between the outer radial portion of the cushion and the cushion cover, to increase the transmission loss of the cushion along a radial direction.

2. The headset of claim 1 further comprising a transducer inside the earcup.

3. The headset of claim 1 wherein the second density is higher than the first density.

4. The headset of claim 1 wherein a second high impedance component is interposed between the inner radial portion of the cushion and the cushion cover.

5. The headset of claim 1 wherein the high impedance component is disposed adjacent the cushion cover.

6. The headset of claim 1 wherein the high impedance component comprises a rigid ring.

7. The headset of claim 1 wherein the high impedance component comprises a colloidal ring.

8. The headset of claim 7 wherein the high impedance component comprises a gel layer.

9. The headset of claim 1 wherein the high impedance component comprises a polyurethane foam.

10. The headset of claim 1 wherein the cushion cover comprises a plurality of openings extending along the inner radial portion of the cushion to acoustically add the volume of the cushion to the volume of the earcup and enhance passive attenuation of the headset.

11. The headset of claim 1 wherein the cushion cover comprises an acoustically transparent mesh along the inner radial portion of the cushion to acoustically add the volume of the cushion to the volume of the earcup and enhance passive attenuation of the headset.

12. The headset of claim 1 wherein the outer radial portion of the cushion has an average area density greater than about 0.03 g/cm$^2$ and the headphone cushion assembly has an axial stiffness per contact area less than about 8 gf/mm/cm$^2$.

13. The headset of claim 1 wherein the headphone cushion assembly has an axial stiffness per contact area less than about 4 gf/mm/cm$^2$.

14. The headset of claim 1 wherein the headphone cushion assembly comprises a toroidal shape.

15. The headset of claim 1 wherein the headphone cushion assembly is circumaural.

16. The headset of claim 1 wherein the headphone cushion assembly is supra-aural.

17. The headset of claim 1 further comprising:

a microphone inside the earcup adjacent to a driver; and active noise reducing circuitry intercoupling the microphone and the driver constructed and arranged to provide active noise cancellation.

18. The headset of claim 17 wherein the inner radial portion of the cushion cover is constructed and arranged to furnish additional damping to help smooth an audio response at an ear of a user and control stability when the headset is not being worn on a head of the user.

19. The apparatus of claim 18 wherein the cushion cover comprises a plurality of openings such that the volume of the cushion is acoustically added to the volume of the earcup.

20. The apparatus of claim 18 wherein the cushion adheres to the cushion cover with a peel strength greater than about 0.1 gf/mm.

21. The apparatus of claim 18 wherein the cushion adheres to the cushion cover with a peel strength greater than about 0.4 gf/mm.

22. The apparatus of claim 18 wherein the cushion comprises open cell foam.

23. The apparatus of claim 18 wherein the cushion has a bulk density between about 2 pcf and about 6 pcf.

24. The apparatus of claim 18 wherein the cushion has an elastic modulus between about 1 kPa and about 10 kPa.

25. The apparatus of claim 18 wherein the cushion has an elastic modulus between about 2 kPa and about 5 kPa.

26. The apparatus of claim 1 wherein the high impedance component comprises a silicone material.

27. A headphone cushion assembly comprising:

a cushion comprising an open cell foam and adapted to be adjacent the ear of the user;

an inner cushion cover substantially covering the inner portion of the cushion adjacent to the ear of the user; the inner cushion cover comprising a plurality of openings, and an outer cushion cover substantially covering the outer part of the cushion away from the ear of the user, the outer cushion cover comprising a first layer having an average area density less than about 0.03 g/cm$^2$ and a second layer attached to the first layer, the second layer having an average density greater than the average area of the first layer and greater than about 0.045 g/cm$^2$.

* * * * *